United States Patent [19]

Henry

[11] 4,108,897
[45] Aug. 22, 1978

[54] BENZYLHYDROXYLAMINE ETHERS

[75] Inventor: Arthur C. Henry, Houston, Tex.

[73] Assignee: Shell Oil Company, Houston, Tex.

[21] Appl. No.: 777,245

[22] Filed: Mar. 14, 1977

[51] Int. Cl.² ............................................. C07C 87/28
[52] U.S. Cl. .......................... 260/570.8 R; 260/455 A;
260/551 C; 260/556 A; 260/562 A; 260/562 P;
260/570.5 P; 260/570.9; 424/330; 560/27
[58] Field of Search ...................... 260/570.8 R, 570.9

[56] References Cited
U.S. PATENT DOCUMENTS 3,245,878  4/1966  Berger et al. .................. 260/570.9 X Primary Examiner—Robert V. Hines

[57] ABSTRACT

Insecticidal benzylhydroxylamine ethers of the formula

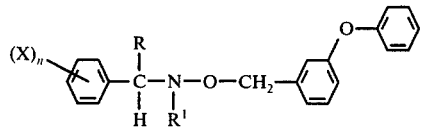

wherein $n$ is 0 or 1, X is lower halogen, R is hydrogen or alkyl of from 1 to 6 carbon atoms, and $R^1$ is hydrogen or alkyl of from 1 to 6 carbon atoms.

1 Claim, No Drawings

BENZYLHYDROXYLAMINE ETHERS

DESCRIPTION OF THE INVENTION

It has been found that useful insecticidal properties are possessed by benzylhydroxylamine ethers of the formula:

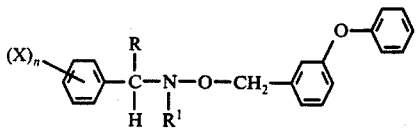

wherein $n$ is 0, 1 or 2, X is lower halogen, R is hydrogen or alkyl of from 1 to 6 carbon atoms, and $R^1$ is hydrogen or alkyl of from 1 to 6 carbon atoms. In these compounds, each alkyl, moiety is either straight-chain or branched-chain in configuration.

For illustration, preparation of typical individual species of the genus defined by Formula I are described in the examples included hereinafter. Other typical, illustrative individual species of this genus are those wherein $R^1$ is hydrogen and $n$ is zero,
  R is methyl;
  R is isopropyl;
  R is tertiary-butyl;
  X is 4-(tertiary-butyl) R, is isopropyl;
  X is 4-bromo, R is isopropyl;
  X is 4-chloro, R is ethyl;
  X is 4-methyl, R is isopropyl;
  X is 4-chloro, R is methyl;
  X is 4-fluoro, R is isopropyl;

Also, individual species wherein X is 4-chloro, R is isopropyl, $R^1$ is isopropyl;
  allyl;
  acetyl;
  methoxycarbonyl.

Compounds of Formula I wherein $R^1$ is hydrogen can be prepared by reduction of the appropriate oxime ether with sodium cyanohydridoborate under acid conditions according to the procedure described by R. F. Borch, et al., J. Am. Chem. Soc., 93, 2897-2904 (1971). In this procedure the oxime is mixed with the borate in a solvent such as methanol, an acid, such as hydrochloric acid, and an indicator which changes color at about pH 4. Since hydrogen ion is consumed during the reaction to maintain the acidic condition of the reaction mixture. The treatment suitably can be carried out at room temperature. The intermediate product thus formed is treated with a base, such as aqueous sodium hydroxide. The desired product can be recovered and purified by conventional techniques, such as extraction, crystallization, chromatography and the like.

Compounds of Formula I wherein $R^1$ represents alkyl, can be prepared by alkylation of the appropriate $R^1$ = hydrogen precursor. This can be accomplished by treating the precursor with a dialkyl sulfate or an $R^1$-halide in the presence of a nitrogen base, such as a tertiary amine, in a solvent such as methylene chloride or toluene, at a moderately elevated temperature, for example about 30°-50°C. The desired product can be recovered by conventional means, for example, by removing the solvent, extracting the residue with a suitable solvent, such as ether, then recovering and purifying the product by crystallization and/or chromatographic techniques.

The precursor oxime ethers can be prepared by treating a stirred mixture of the appropriate oxime and 3-phenoxybenzyl bromide in a solvent, such as tetrahydrofuran, with sodium hydride. The reaction suitably can be conducted at or somewhat above room temperature, for example 15°-70°C. Since the reaction generally is exothermic, it ususally will be found desirable to add the sodium hydride slowly, cooling the reaction mixture as necessary to maintain its temperature at the desired level. The desired product can be recovered by filtering the by-product sodium bromide, evaporating the solvent from the filtrate, then employing conventional techniques, such as selective extraction, recrystallization and/or chromatography, to isolate the product.

3-phenoxybenzyl bromide is a known compound: Belgian Pat. No. 809,867.

The precursor oximes can be prepared by procedures set forth in Organic Syntheses, Collective Volume 2, pages 70-72, by mixing the appropriate ketone with hydroxylamine hydrochloride in a solvent such as aqueous methanol or ethanol, then treating the mixture with sodium hydroxide at room temperature or somewhat above, then treating the resulting mixture with dilute hydrochloric acid, and recovering the oxime by conventional techniques.

The precursor ketones wherein X is not hydrogen can be prepared by suitable conventional methods, such as Friedel-Crafts acylation of the appropriate benzene, $(X)_n$benzene, with the appropriate acid chloride, RC(O)Cl, using aluminum trichloride as catalyst or by treating a Grignard reagent of the appropriate R-bromide with the appropriate $(X)_n$benzonitrile in the presence of ether as solvent at a temperature of from about 20° C to reflux, then treating the resulting mixture with dilute sulfuric acid and recovering the desired product by conventional means.

These procedures for preparing compounds of this invention are illustrated in Examples 1 and 2, following. In all cases, the identities of the products, and of the precursors involved were confirmed by appropriate chemical and spectral analyses.

EXAMPLE 1

4-chloro-alpha-(1-methylethyl)-N-((3-phenoxyphenyl)-methoxy)benzenemethanamine (1)

133.35 g of aluminum chloride and 500 ml of chlorobenzene were mixed, and at room temperature 106 g of isobutyryl chloride was added over a 7-minute period, with cooling to maintain the reaction mixture temperature. The mixture was stirred about 5 hours at room temperature, then poured into an ice-water mixture. The resulting mixture was extracted with methylene chloride; the extract was washed with water, dried (MgSO$_4$) and stripped of solvent under reduced pressure. The liquid residue was distilled to give 4-chloroisobutyrophenone, (1A) as a liquid, b.p.: 101°, 0.2 Torr.

91 g of 1A, 200 ml of ethanol and 40 ml of water were mixed, 60 g of hydroxylamine hydrochloride was added and then 110 g of sodium hydroxide was added over a 10-minute period. The mixture was stirred at room temperature for 1.5 hours, then at reflux for 0.5 hour, cooled, added to cold dilute hydrochloric acid and filtered. The filtrate was dried (MgSO$_4$) and stripped of solvent. The solid residue was crystallized from hexane containing a trace of ether to give 1-(4-chlorophenyl)-2-methyl-1-propanone oxime (1B), m.p.: 91°–117°.

3.86 g of 1B, 5.2 g of 3-phenoxybenzyl bromide and 30 ml of tetrahydrofuran were mixed and 0.9 g of sodium hydride was added. The mixture was heated to 35°. The mixture was cooled, stirred at room temperature for 21 hours, then filtered, and the solvent was stripped from the filtrate. The liquid residue was chromatographed (silica gel, ½ v/v methylene chloride/pentane) to give (1C), 1-(4-chlorophenyl)-2-methyl-1-propanone O-((3-phenoxyphenyl)methyl)oxime as a light yellow liquid, boiling point not determined.

2.7 g of 1C, 0.23 g of sodium cyanohydridoborate, 6 ml of 2 N hydrochloric acid in methanol and a few crystals of bromocresol green were mixed and the mixture was stirred at room temperature for 21 hours, sufficient additional acidic methanol being added as necessary to maintain a yellow color in the mixture. The solvent was stripped. To the residue was added 4 ml of water and sufficient 6 N sodium hydroxide solution saturated with sodium chloride to provide a mixture pH of 10. The mixture was stirred for 10 minutes at room temperature and extracted with methylene chloride. The extract was dried ($MgSO_4$) and stripped of solvent. An equivalent amount of the borate, the acidic methanol and indicator were added, and the treatment and work-up were repeated. The product was chromatographed over silica gel, using as eluent methylene chloride containing initially an equal volume of pentane, the pentane content being gradually reduced to zero. 1 was obtained as a liquid, boiling point not determined.

EXAMPLE 2

4-chloro-N-methyl-alpha-(1-methylethyl)-N-(3-phenoxyphenyl)methoxy)benzenemethanamine (2)

A mixture of 3.82 g of 1, 1.3 of dimethyl sulfate, 1.3 g of N,N-diisopropylethylamine and 35 ml of methylene chloride was refluxed for 22 hours, then stripped of solvent. The residue was triturated with ether and the solid phase was filtered. The filtrate was stripped of solvent and the residue was chromatographed using methylene chloride as eluent to give 2, as a liquid, boiling point not determined.

The compounds of this invention exhibit useful insecticidal activity, being of particular interest for control of the larval "caterpillar" or "worm" forms of lepidopterous insects of the genus Heliothis, such as H. zea (corn earworm, cotton bollworm, tomato fruitworm), *H. virescens* (tobacco budworm); the genus Agrotis, such as *A. ipsilon* (black cutworm); the genus Trichoplusia, such as *T. ni* (cabbage looper), and the genus Spodoptera, such as *S. littoralis* (Egyptian cotton leafworm).

The activity of Compounds 1 and 2 with respect to insects were determined by using standardized test methods to establish the $LC_{50}$ dosage (in milligrams of test compound per 100 milliliters of solvent or liquid carrier required in the solution or suspension of test compound used) that was required to kill 50% of the test insects. The test insects were the housefly, corn earworm, pea aphid and 2-spotted mite. Activity with respect to mosquito larvae was determined by placing the larvae in water containing the test compound.

Compound 1 was active with respect to the houseflies, pea aphids and corn earworms; it was not, or only slightly active with respect to the mosquito larvae and mites. Compound 2 was active only with respect to the corn earworms.

The invention includes within its scope a carrier, optionally a surface-active agent — and, as active ingredient, at least one insecticide of this invention. Likewise the invention includes also a method of combatting insect pests at a locus which comprises applying to the locus an effective amount of at least one insecticide of the invention.

The term "carrier" as used herein means a material which may be inorganic or organic and of synthetic or natural origin with which the active compound is mixed or formulated to facilitate its application to the plant, seed, soil or other object to be treated, or its storage, transport or handling. The carrier may be a solid or a liquid.

Suitable solid carriers may be natural and synthetic clays and silicates, for example, natural silicas such as diatomaceous earths; magnesium silicates, for example, talcs; magnesium aluminum silicates, for example, attapulgites and vermiculities; aluminum silicates, for example, kaolinites, montmorillonites and micas; calcium carbonate; calcium sulfate; synethetic hydrated silicon oxides and synthetic calcium or aluminum silicates; elements such as for example, carbon and sulfur; natural and synthetic resins such as, for example, coumarone resins, polyvinyl chloride and styrene polymers and copolymers; solid polychlorophenols; bitumen, waxes such as beeswax paraffin wax, and chlorinated mineral waxes; degradeable organic solids, such as ground corn cobs and walnut shells; and solid fertilizers, for example, superphosphates.

Suitable liquid carriers include solvents for the compounds of this invention and liquids in which the toxicant is insoluble or only slightly soluble.

Examples of such solvents and liquid carriers generally are water, alcohols, for example, isopropyl alcohol; ketones, such as acetone, methyl ethyl ketone, methyl isobutyl ketone and cyclohexanone; ethers; aromatic hydrocarbons such as benzene, toluene and xylene; petroleum fractions, such as kerosene, light mineral oils; chlorinated hydrocarbons, such as carbon tetrachloride, perchlorethylene, trichloroethane; including liquified normally vaporous gaseous compounds. Mixtures of different liquids are often suitable.

If used, the surface-active agent may be an emulsifying agent or a dispersing agent or a wetting agent. It may be nonionic or ionic. Surface-active agents usually applied in formulating pesticides may be used. Examples of such surface-active agents are the sodium or calcium salts of polyacrylic acids and lignin sulfonic acids; the condensation products of fatty acids or aliphatic amines or amides containing at least 12 carbon atoms in the molecule with ethylene oxide and/or propylene oxide; fatty acid esters of glycerol, sorbitan, sucrose or pentaerythritol; fatty acid salts of low molecular weight, mono-, di- and trialkylamines; condensates of these with ethylene oxide and/or propylene oxide; condensation products of fatty alchols or alkyl phenols, for example, p-octylphenol or p-octylcresol, with ethylene oxide and/or propylene oxide; sulfates or sulfonates of these condensation products; alkali or alkaline earth metal salts, preferably sodium salts, of sulfuric or sulfonic acids esters containing at least 10 carbon atoms in the molecule, for example, sodium lauryl sulfate, sodium secondary alkyl sulfates, sodium salts of sulfonated caster oil, and sodium alkylaryl sulfonates such as sodium dodecylbenzene sulfonate; and polymers of ethylene oxide and copolymers of ethylene oxide and copolymers of ethylene oxide and propylene oxide.

The compositions of the invention may be formulated as wettable powders, dusts, granules, solutions, emulsifiable concentrates, emulsions, suspension concentrates or aerosols. Encapsulated formulations and controlled release formulations also are contemplated, as are bait formulations. wettable powders are usually compounded to contain 25, 50 or 75%w of toxicant and usually contain, in addition to solid carrier, 3–10%w of stabilizer (s) and/or other additives such as penetrants or stickers. Dusts are usually formulated as a dust concentrate having a similar composition to that of a wettable powder, but without a dispersant, and are diluted in the field with further solid carrier to give a composition usually containing ½–10%w of active ingredient. Granules may be manufactured by agglomeration or impregnation techniques. Generally, granules will contain ½–25%w active ingredient and 0–10%w of additives such as stabilizers, slow release modifiers and binding agents. Emulsifiable concentrates usually contain, in addition to the solvent, and when necessary, co-solvent, 10–50%w/v active ingredient, 2–20%w/v emulsifiers and 0–20%w/v of appropriate additives such as stabilizers, penetrants and corrosions inhibitors. Suspension concentrates are compounded so as to obtain a stable, non-sedimenting, flowable product and usually contain 10–75%w active ingredient, 0–5%w of dispersing agents, 0.1–19%w of suspending agents such as protective colloids and thixotropic agents, 0–19%w of appropriate additives such as defoamers, corrosion inhibitors, stabilizers, penetrants and stickers, and as carrier, water or an organic liquid in which the active ingredient is substantially insoluble; certain organic additives or inorganic salts may be dissolved in the carrier to assist in preventing sedimentation or as antifreeze agents for water.

Aqueous dispersions and emulsions, for example, compositions obtained by diluting a wettable powder or an emulsifiable concentrate according to the invention with water, also lie within the scope of the present invention.

The compositions of the invention may also contain other ingredients, for example, other compounds possessing pesticidal, herbicidal or fungicidal properties, or attractants, such as pheromones, attractive food ingredients, and the like, for use in baits and trap formulations.

These compositions are applied in sufficient amount to supply the effective dosage of active ingredient at the focus to be protected. This dosage is dependent upon many factors, including the carrier employed, the method and conditions for application, whether the formulation is present at the locus in the form of an aerosol, or as a film, or as discrete particles, the thickness of film or size of particles, the insect species to be controlled and the like, proper consideration and resolution of these factors to provide the necessary dosage of the active ingredient at the locus being within the skill of those versed in the art. In general, however, the insecticidal formulation is applied to the foliage of the plants to be protected to provide the effective dosage of the compound of this invention at the locus to be protected — i.e., the dosage to which the insect contacts — is of the order of 0.001% to 0.5% based on the total weight of the formulation, though under some circumstances the effective concentration will be as little as 0.001% or as much as 2%, on the same basis.

What is claimed is:

1. A compound of the formula:

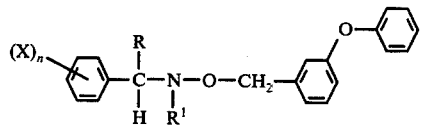

wherein $n$ is 0 or 1, $X$ is lower halogen, $R$ is hydrogen or alkyl of from 1 to 6 carbon atoms, and $R^1$ is hydrogen or alkyl of from 1 to 6 carbon atoms.

* * * * *

UNITED STATES PATENT AND TRADEMARK OFFICE
CERTIFICATE OF CORRECTION

PATENT NO. : 4,108,897
DATED : August 22, 1978
INVENTOR(S) : ARTHUR C. HENRY

It is certified that error appears in the above–identified patent and that said Letters Patent are hereby corrected as shown below:

Column 1, line 16, change "0, 1 or 2," to -- 0 or 1, --.

Column 1, between lines 29 and 30, insert -- n is 1, --.

Signed and Sealed this

Thirteenth Day of January 1981

[SEAL]

Attest:

SIDNEY A. DIAMOND

Attesting Officer    Commissioner of Patents and Trademarks